(12) United States Patent
Roessler et al.

(10) Patent No.: US 10,228,370 B2
(45) Date of Patent: Mar. 12, 2019

(54) **RECOMBINANT *TRYPANOSOMA CRUZI* JL7 ANTIGEN VARIANTS AND THEIR USE FOR DETECTING CHAGAS DISEASE**

(71) Applicant: Roche Diagnostics Operations, Inc., Indianapolis, IN (US)

(72) Inventors: Dieter Roessler, Kirchseeon (DE); Barbara Upmeier, Iffeldorf (DE); Toralf Zarnt, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/587,907

(22) Filed: May 5, 2017

(65) Prior Publication Data

US 2017/0248598 A1    Aug. 31, 2017

Related U.S. Application Data

(63) Continuation of application No. PCT/EP2015/075692, filed on Nov. 4, 2015.

(30) Foreign Application Priority Data

Nov. 6, 2014   (EP) .................................. 14192004
Mar. 27, 2015   (EP) .................................. 15161274

(51) Int. Cl.
   *G01N 33/569*   (2006.01)
   *C07K 14/44*   (2006.01)
   *G01N 33/564*   (2006.01)

(52) U.S. Cl.
   CPC ....... *G01N 33/56905* (2013.01); *C07K 14/44* (2013.01); *G01N 33/564* (2013.01); *C07K 2319/21* (2013.01); *C07K 2319/40* (2013.01); *C07K 2319/70* (2013.01); *G01N 2333/44* (2013.01); *G01N 2469/20* (2013.01); *G01N 2800/26* (2013.01)

(58) Field of Classification Search
   None
   See application file for complete search history.

(56) References Cited

U.S. PATENT DOCUMENTS

| 8,329,411 B2 | 12/2012 | Tarleton et al. |
| 2010/0196933 A1 | 8/2010 | Kirchhoff et al. |

FOREIGN PATENT DOCUMENTS

| EP | 0976763 B1 | 11/2003 |
| WO | 2009/017736 A1 | 2/2009 |
| WO | 2010/142829 A1 | 12/2010 |

OTHER PUBLICATIONS

Bottino, Carolina G. et al., Chagas disease-specific antigens: characterization of epitopes in CRA/FRA by synthetic peptide mapping and evaluation by ELISA-peptide assay, BMC Infectious Diseases, 2013, 10 pps., vol. 13, No. 568.

Camussone, Cecilia et al., Comparison of Recombinant Trypanosoma cruzi Peptide Mixtures versus Multiepitope Chimeric Proteins as Sensitizing Antigens for Immunodiagnosis, Clinical and Vaccine Immunology, 2009, pp. 899-905, vol. 16, No. 6.

Chiaramonte, M. G. et al., Polymerase chain reaction reveals Trypanosoma cruzi infection suspected by serology in cutaneous and mucocutaneous leishmaniasis patients, Acta Tropica, 1999, pp. 295-308, vol. 72.

Cotrim, Paulo C. et al., Organization and expression of the gene encoding an immunodominant repetitive antigen associated to the cytoskeleton of Trypanosoma cruzi, Molecular and Biochemical Parasitology, 1995, pp. 89-98, vol. 71.

Da Silveira, José Franco et al., Chagas Disease: recombinant Trypanosoma cruzi antigens for serological diagnosis, Trends in Parasitology, 2001, pp. 286-291, vol. 17, No. 6.

Fernández-Villegas, Ana et al., Short-term follow-up of chagasic patients after benznidazole treatment using multiple serological markers, BMC Infectious Diseases, 2011, 7 pages, vol. 11, No. 206.

International Search Report dated Jan. 14, 2016, in Application No. PCT/EP2015/675692, 4 pages.

Longhi, Silvia A. et al., Short Report: Evaluation of In-House ELISA Using Trypanosoma cruzi Lysate and Recombinant Antigens for Diagnosis of Chagas Disease and Discrimination of Its Clinical Forms, American J. Trop. Med. Hyg., 2012, pp. 267-271, vol. 87, No. 2.

Marcipar, Iván S. and Lagier, Claudia M., Advances in Serological Diagnosis of Chagas' Disease by Using Recombinant Proteins, Current Topics in Tropical Medicine, 2012, pp. 273-298.

Thomas, M. C. et al., Mapping of the antigenic determinants of the T. cruzi kinetoplastid membrane protein-11. Identification of a linear epitope specifically recognized by human Chagasic sera, Clinical and Experimental Immunology, 2001, pp. 465-471, vol. 123.

Umezawa, Eufrosina S. et al., An improved serodiagnostic test for Chagas' disease employing a mixture of Trypanosoma cruzi recombinant antigens, Transfusion, 2003, pp. 91-97, vol. 43.

(Continued)

*Primary Examiner* — Padmavathi Baskar
(74) *Attorney, Agent, or Firm* — Roche Diagnostics Operations, Inc.

(57) ABSTRACT

The invention concerns variants of JL7 antigens that are suitable for detecting antibodies against *Trypanosoma cruzi* (causing Chagas disease) in an isolated biological sample. These antigens comprise a JL7 specific amino acid sequence, said JL7 specific sequence consisting of two copies of SEQ ID NO. 2, wherein each of said two copies has an amino acid identity of at least 90% to SEQ ID NO.2 and wherein no further *Trypanosoma cruzi* specific amino acid sequences are present in said polypeptide. The invention also concerns a composition of polypeptides useful for the detection of antibodies against *Trypanosoma cruzi* that comprises the above characterized JL7 antigen along with at least one of *T. cruzi* polypeptides 1F8, Cruzipain, KMP-11 and PAR-2. Moreover, it relates to a method for producing JL7 antigen as well as to diagnostic methods for detecting *T. cruzi* antibodies using the JL7 polypeptide. In addition, the invention concerns a reagent kit comprising said JL7 polypeptides or composition of *Trypanosoma cruzi* polypeptides.

3 Claims, 2 Drawing Sheets

Specification includes a Sequence Listing.

(56) References Cited

OTHER PUBLICATIONS

Umezawa, Eufrosina S. et al., Evaluation of Recombinant Antigens for Serodiagnosis of Chagas' Disease in South and Central America, Journal of Clinical Microbiology, 1999, pp. 1554-1560, vol. 37, No. 5.

Valiente-Gabioud, Ariel A. et al., Effect of repetitiveness on the immunogenicity and antigenicity of Trypanosoma cruzi FRA protein, Experimental Parasitology, 2011, pp. 672-679, vol. 127, No. 3.

Repeat 1   MEQERRQLLEKDPRRNAREIAALEESMNARAQELAREKKLADRAFLDQKPEGVPLRELPLDDDSDFVA   68
Repeat 2   MEQERRQLLEKDPRRNAKEIAALEESMNARAQELAREKKLADRAFLDQKPEGVPLRELPLDDDSDFVS   68
Repeat 3   MEQERRQLLEKDPRRNVQKIADLEESMNARAQELAREKKLADRAFLDQKPEGVSLRELPLDDDSDFVS   68
Repeat 4   MEQERRQLLEKDPRKNVQIYAD                                                22

JL7

JL7short1

JL7short2

JL7short1+2

JL7short3+4

JL7short3

SEQUENCE LISTING

```
<160> NUMBER OF SEQ ID NOS: 7

<210> SEQ ID NO 1
<211> LENGTH: 226
<212> TYPE: PRT
<213> ORGANISM: Trypanosoma cruzi

<400> SEQUENCE: 1

Met Glu Gln Glu Arg Arg Gln Leu Leu Glu Lys Asp Pro Arg Arg Asn
1               5                   10                  15

Ala Arg Glu Ile Ala Ala Leu Glu Glu Ser Met Asn Ala Arg Ala Gln
            20                  25                  30

Glu Leu Ala Arg Glu Lys Lys Leu Ala Asp Arg Ala Phe Leu Asp Gln
        35                  40                  45

Lys Pro Glu Gly Val Pro Leu Arg Glu Leu Pro Leu Asp Asp Asp Ser
    50                  55                  60

Asp Phe Val Ala Met Glu Gln Glu Arg Arg Gln Leu Leu Glu Lys Asp
65                  70                  75                  80

Pro Arg Arg Asn Ala Lys Glu Ile Ala Ala Leu Glu Glu Ser Met Asn
                85                  90                  95

Ala Arg Ala Gln Glu Leu Ala Arg Glu Lys Lys Leu Ala Asp Arg Ala
            100                 105                 110
```

Phe Leu Asp Gln Lys Pro Glu Gly Val Pro Leu Arg Glu Leu Pro Leu
            115                 120                 125

Asp Asp Asp Ser Asp Phe Val Ser Met Glu Gln Glu Arg Arg Gln Leu
        130                 135                 140

Leu Glu Lys Asp Pro Arg Arg Asn Val Gln Lys Ile Ala Asp Leu Glu
145                 150                 155                 160

Glu Ser Met Asn Ala Arg Ala Gln Glu Leu Ala Arg Glu Lys Lys Leu
                165                 170                 175

Ala Asp Arg Ala Phe Leu Asp Gln Lys Pro Glu Gly Val Ser Leu Arg
            180                 185                 190

Glu Leu Pro Leu Asp Asp Asp Ser Asp Phe Val Ser Met Glu Gln Glu
        195                 200                 205

Arg Arg Gln Leu Leu Glu Lys Asp Pro Arg Lys Asn Val Gln Ile Val
    210                 215                 220

Ala Asp
225

<210> SEQ ID NO 2
<211> LENGTH: 68
<212> TYPE: PRT
<213> ORGANISM: Trypanosoma cruzi

<400> SEQUENCE: 2

Met Glu Gln Glu Arg Arg Gln Leu Leu Glu Lys Asp Pro Arg Arg Asn
1               5                   10                  15

Ala Lys Glu Ile Ala Ala Leu Glu Glu Ser Met Asn Ala Arg Ala Gln
            20                  25                  30

Glu Leu Ala Arg Glu Lys Lys Leu Ala Asp Arg Ala Phe Leu Asp Gln
        35                  40                  45

Lys Pro Glu Gly Val Pro Leu Arg Glu Leu Pro Leu Asp Asp Asp Ser
    50                  55                  60

Asp Phe Val Ala
65

<210> SEQ ID NO 3
<211> LENGTH: 68
<212> TYPE: PRT
<213> ORGANISM: Trypanosoma cruzi

<400> SEQUENCE: 3

Met Glu Gln Glu Arg Arg Gln Leu Leu Glu Lys Asp Pro Arg Arg Asn
1               5                   10                  15

Ala Lys Glu Ile Ala Ala Leu Glu Glu Ser Met Asn Ala Arg Ala Gln
            20                  25                  30

Glu Leu Ala Arg Glu Lys Lys Leu Ala Asp Arg Ala Phe Leu Asp Gln
        35                  40                  45

Lys Pro Glu Gly Val Pro Leu Arg Glu Leu Pro Leu Asp Asp Asp Ser
    50                  55                  60

Asp Phe Val Ser
65

<210> SEQ ID NO 4
<211> LENGTH: 136
<212> TYPE: PRT
<213> ORGANISM: Trypanosoma cruzi

<400> SEQUENCE: 4

Met Glu Gln Glu Arg Arg Gln Leu Leu Glu Lys Asp Pro Arg Arg Asn
1               5                   10                  15

Ala Arg Glu Ile Ala Ala Leu Glu Glu Ser Met Asn Ala Arg Ala Gln
            20                  25                  30

Glu Leu Ala Arg Glu Lys Lys Leu Ala Asp Arg Ala Phe Leu Asp Gln
        35                  40                  45

Lys Pro Glu Gly Val Pro Leu Arg Glu Leu Pro Leu Asp Asp Asp Ser
    50                  55                  60

Asp Phe Val Ala Met Glu Gln Glu Arg Arg Gln Leu Leu Glu Lys Asp
65                  70                  75                  80

Pro Arg Arg Asn Ala Lys Glu Ile Ala Ala Leu Glu Glu Ser Met Asn
                85                  90                  95

Ala Arg Ala Gln Glu Leu Ala Arg Glu Lys Lys Leu Ala Asp Arg Ala
            100                 105                 110

Phe Leu Asp Gln Lys Pro Glu Gly Val Pro Leu Arg Glu Leu Pro Leu
        115                 120                 125

Asp Asp Asp Ser Asp Phe Val Ser
    130                 135

<210> SEQ ID NO 5
<211> LENGTH: 90
<212> TYPE: PRT
<213> ORGANISM: Trypanosoma cruzi

<400> SEQUENCE: 5

Met Glu Gln Glu Arg Arg Gln Leu Leu Glu Lys Asp Pro Arg Arg Asn
1               5                   10                  15

Val Gln Lys Ile Ala Asp Leu Glu Glu Ser Met Asn Ala Arg Ala Gln
            20                  25                  30

Glu Leu Ala Arg Glu Lys Lys Leu Ala Asp Arg Ala Phe Leu Asp Gln
        35                  40                  45

Lys Pro Glu Gly Val Ser Leu Arg Glu Leu Pro Leu Asp Asp Asp Ser
    50                  55                  60

Asp Phe Val Ser Met Glu Gln Glu Arg Arg Gln Leu Leu Glu Lys Asp
65                  70                  75                  80

Pro Arg Lys Asn Val Gln Ile Val Ala Asp
                85                  90

<210> SEQ ID NO 6
<211> LENGTH: 68
<212> TYPE: PRT
<213> ORGANISM: Trypanosoma cruzi

<400> SEQUENCE: 6

Met Glu Gln Glu Arg Arg Gln Leu Leu Glu Lys Asp Pro Arg Arg Asn
1               5                   10                  15

Val Gln Lys Ile Ala Asp Leu Glu Glu Ser Met Asn Ala Arg Ala Gln
            20                  25                  30

Glu Leu Ala Arg Glu Lys Lys Leu Ala Asp Arg Ala Phe Leu Asp Gln
        35                  40                  45

Lys Pro Glu Gly Val Ser Leu Arg Glu Leu Pro Leu Asp Asp Asp Ser
    50                  55                  60

Asp Phe Val Ser
65

<210> SEQ ID NO 7
<211> LENGTH: 15

```
<212> TYPE: PRT
<213> ORGANISM: Artificial Sequence
<220> FEATURE:
<223> OTHER INFORMATION: Hexa-histidine tag

<400> SEQUENCE: 7

Gly Gly Gly Ser Gly Gly Gly Leu Glu His His His His His His
1               5                   10                  15
```

RECOMBINANT *TRYPANOSOMA CRUZI* JL7 ANTIGEN VARIANTS AND THEIR USE FOR DETECTING CHAGAS DISEASE

CROSS-REFERENCE TO RELATED APPLICATIONS

This application is a continuation of International Application No. PCT/EP2015/075692 filed Nov. 4, 2015, which claims priority to European Application Nos. 14192004.1 filed Nov. 6, 2014 and 15161274.4 filed Mar. 27, 2015, the disclosures of which are hereby incorporated by reference in their entirety.

BACKGROUND OF THE DISCLOSURE

*Trypanosoma cruzi* is a flagellate protozoan that causes a tropical parasitic disease called Chagas disease. In the course of Chagas disease the infected patient typically passes an acute phase followed by a chronic phase with varying symptoms ranging between mild and life-threatening. Only in the initial phase the patient is responsive to antiparasitic treatment. Some patients develop cardiac or intestinal complications leading to death.

*T. cruzi* is commonly transmitted to humans and other mammals by an insect vector, the blood-sucking "kissing bugs" of the subfamily Triatominae (family Reduviidae; in German: "Raubwanzen"). The disease may also be spread through blood transfusion and organ transplantation, ingestion of food contaminated with parasites, and from a mother to her fetus. To prevent further spread of Chagas disease it is important to screen blood donations and medical products based on blood for the presence of the parasite and for antibodies against *T. cruzi*, in particular in mainly infected territories like Mexico, Central and South America and in the Southern United States.

Currently, several serologic diagnostic methods are available to detect infections with *T. cruzi,* e.g. detection of antibodies against *T. cruzi* by indirect immunofluorescence, indirect hemagglutination, complement fixation, immunoblot techniques and ELISAs. Also methods of molecular biology (e.g. PCR) and elaborate xenodiagnostic methods are applied. In xenodiagnostics a vector-transmitted infection a laboratory-reared, pathogen-free insect (here: the kissing bug) is allowed to suck blood from a patient. The intestinal contents of the insect are then examined for the presence of the pathogen (here: *Trypanosoma cruzi*).

Each of these methods shows its own weaknesses and strengths with regard to sensitivity and specificity and accordingly there is no gold standard method available so far.

In the beginning of Chagas assay development for detection of antibodies native antigen lysates were applied and are still being used. However, using lysates only one of the three development stages of *T. cruzi* is represented in this antigen composition so that there is a certain likelihood to miss infections of the two other stages. More modern assays apply mixtures of recombinant antigens, representing all stages of *T. cruzi* infection.

Serological assays for detecting antibodies against *Trypanosoma cruzi* antigens have been widely described in prior art literature. For example Silveira et al. (Trends in Parasitology 2001, Vol. 17 No. 6, p. 286-291) describes *T. cruzi* recombinant antigens relevant for serodiagnosis have been isolated by several laboratories. Several of these genes have tandemly repeated sequences resulting in proteins showing repeated amino acid sequence motifs.

One of the antigens that is widely used in serological assays for detection of antibodies against *T. cruzi* is JL7, UniProt database entry no. Q4CS87, also described by the synonyms FRA, Agl and H49 (for review see e.g. Cotrim et al. 1995, Mol Biochem Parasitol 71, 89-98 and Umezawa et al. 1999, J Clin Microbiol, 1554-1560). Also Silveira et al. (supra) describe FRA (JL7) in several mixture of various additional *T. cruzi* antigens for use in ELISA assays. No specific JL7-related polypeptides are disclosed.

Valiente-Gabioud et al. (Exp. Parasitol. 2011, 127, p. 672-679) discuss the effect of repetitiveness on the immunogenicity and antigenicity of *T. cruzi* FRA (JL7) protein. It is recommended to use four repetitive repeats to get satisfying ELISA signals from human infected sera. The problem of assay specificity is not addressed and no specific JL7 polypeptides are disclosed.

All antigen variants based on the above mentioned JL7 sequence harbor repeats of 68 amino acids that are highly conserved between strains and isolates of *T. cruzi*. JL7 is a putative calpain cysteine peptidase of 226 amino acids comprising about 3.5 repeats of said motif of 68 amino acids (see FIG. 1). However, antigens harboring several identical or very similar repeats are often prone to interferences caused by non-specific binding of IgM or IgG molecules or rheumatic factors present in a sample to be analyzed for the presence of anti-*T. cruzi* antibodies.

The problem therefore can be seen in providing a recombinant JL7 antigen composition and diagnostic method for detecting infections with *Trypanosoma cruzi* that overcome the disadvantages with respect to interference susceptibility.

The problem is solved by the current invention as specified in the claims. The claimed antigens and compositions as well as diagnostic methods provide an immunodiagnostic solution with high specificity and sensitivity and reliable reproducibility.

SUMMARY OF THE INVENTION

The present invention concerns variants of JL7 antigens that are suitable for detecting antibodies against *Trypanosoma cruzi* JL7 antigen in an isolated biological sample. These antigens comprise a JL7 specific amino acid sequence, said JL7 specific sequence consisting of two copies of SEQ ID NO. 2, wherein each of said two copies has an amino acid identity of at least 90% to SEQ ID NO. 2 and wherein no further *Trypanosoma cruzi* specific amino acid sequences are present in said polypeptide. The invention also concerns a composition of polypeptides useful for the detection of antibodies against *Trypanosoma cruzi* that comprises the above characterized JL7 antigen along with at least one of *T. cruzi* polypeptides 1F8, Cruzipain, KMP-11 and PAR-2. Moreover, the invention relates to a method for producing JL7 antigen as well as to diagnostic methods for detecting *T. cruzi* antibodies using the JL7 polypeptide. In addition, the invention concerns a reagent kit comprising said JL7 polypeptides or composition of *Trypanosoma cruzi* polypeptides.

Legend to the Disclosed Amino Acid Sequences

SEQ ID NO. 1 shows a partial sequence of *T. cruzi* protein JL7 (UniProt entry Q4CS87), also known as FRA, Agl, H49; full descriptive name: calpain cysteine peptidase, putative. SEQ ID NO. 1 shows amino acid positions 62-287 of the above UniProt database entry, resulting in a polypeptide with a length of 226 amino acids. The full length protein comprises amino acids 1 to 1275.

MEQERRQLLE KDPRRNAREI AALEESMNAR AQELAREKKL

ADRAFLDQKP EGVPLRELPL DDDSDFVAME QERRQLLEKD

PRRNAKEIAA LEESMNARAQ ELAREKKLAD RAFLDQKPEG

VPLRELPLDD DSDFVSMEQE RRQLLEKDPR RNVQKIADLE

ESMNARAQEL AREKKLADRA FLDQKPEGVS LRELPLDDDS

DFVSMEQERR QLLEKDPRKN VQIVAD

SEQ ID NO. 2 shows antigen JL7short1, also shown as amino acid positions 1-68 of SEQ ID NO.1

MEQERRQLLE KDPRRNAKEI AALEESMNAR AQELAREKKL
ADRAFLDQKP EGVPLRELPL DDDSDFVA

SEQ ID NO. 3 shows antigen JL7short2, also shown as amino acid positions 69-136 of SEQ ID NO.1

MEQERRQLLE KDPRRNAKEI AALEESMNAR AQELAREKKL
ADRAFLDQKP EGVPLRELPL DDDSDFVS

SEQ ID NO. 4 shows antigen JL7short1+2 which corresponds to a combination of SEQ ID NOs. 2 and 3, also shown as amino acid positions 1-136 of SEQ ID NO.1

MEQERRQLLE KDPRRNAREI AALEESMNAR AQELAREKKL

ADRAFLDQKP EGVPLRELPL DDDSDFVAME QERRQLLEKD

PRRNAKEIAA LEESMNARAQ ELAREKKLAD RAFLDQKPEG

VPLRELPLDD DSDFVS

SEQ ID NO. 5 shows antigen JL7short3+4 which corresponds to amino acid positions 137-226 of SEQ ID NO.1

MEQERRQLLE KDPRRNVQKI ADLEESMNAR AQELAREKKL
ADRAFLDQKP EGVSLRELPL DDDSDFVSME QERRQLLEKD
PRKNVQIVAD

SEQ ID NO. 6 shows antigen JL7short3 which corresponds to amino acid positions 137-204 of SEQ ID NO.1

MEQERRQLLE KDPRRNVQKI ADLEESMNAR AQELAREKKL
ADRAFLDQKP EGVSLRELPL DDDSDFVS

SEQ ID NO. 7 shows a hexa-histidine tag that can be added to the N-terminal or preferably to the C-terminal end the polypeptides according to the invention. The tag is used to facilitate protein purification.

GGGSGGGLEH HHHHH

DETAILED DESCRIPTION OF THE INVENTION

The properties of *T. cruzi* JL7 antigen and its amino acid sequence have been widely described in the state of the art. However, the problem of increased susceptibility to interference of diagnostic *T. cruzi* assays that is caused by antigens with multiple repeats has not been addressed sufficiently. The high vulnerability to interference can lead to false positive results when for example a non-specific IgM molecule or a non-specific IgG together with a rheumatic factor present in a sample to be analyzed produces a positive test result, pretending that anti-*T. cruzi* antibodies are present in a sample whereas in reality the sample should be detected as negative. False-positive results lead to an undesired decrease of assay specificity. However, in diagnostic methods for infectious diseases parameters regulatory authorities request a high degree of specificity.

Surprisingly, we have identified JL7 variants that on the one hand do still possess sufficient antigenic properties to be bound by sample antibodies and on the other hand do not lead to false-positive results. The complete JL7 polypeptide harbors about 3.5 repeats of a motif of 68 amino acids. The question was whether one repeat would be sufficient to provide a suitable diagnostic rare reagent. When repeats 1 and 2 (designated as JL7short1, SEQ ID NO. 2 and JL7short2, SEQ ID NO. 3, respectively) were expressed as separate antigens none of the shortened variants was able to detect all of the positive samples correctly (Table 2). The same was true for a shortened variant consisting of about 1.5 repeats, called JL7short3+4 (shown in SEQ ID NO. 5). However, when two repeats of said 68 amino acid motif were put together adjacently such as in SEQ ID NO. 4 samples that had been initially diagnosed as positive using a complete JL7 polypeptide harboring 3.5 repeats turned out to be in fact false positive samples. On the other hand, said JL7 polypeptide having two repeats of a 68 amino acid repeat as shown in SEQ ID NO. 2 were able to reliably detect real positive samples correctly as positive, i.e. as to contain antibodies against *T. cruzi*.

The invention therefore concerns a polypeptide suitable for detecting antibodies against *Trypanosoma cruzi* JL7 antigen in an isolated biological sample comprising a JL7 specific amino acid sequence, said JL7 specific sequence consisting of two copies of SEQ ID NO. 2, wherein each of said two copies has an amino acid identity of at least 90% to SEQ ID NO. 2 and wherein no further *Trypanosoma cruzi* specific amino acid sequences are present in said polypeptide. According to the invention the two copies of SEQ ID NO. 2 can be directly adjacent to each other so that no additional amino acid is present between the two copies. As an alternative they can be separated by a linker sequence that is not present in the JL7 specific sequence.

Figure 1:
FIG. 1 Structure of repeats in complete JL7 amino acid sequence. Upper section: All four repeats are aligned showing amino acid identity (bold letters) and differences (normal underlined letters). Lower section: schematic drawing of JL7 variants and relative position of their repeat domain(s). JL7short1+2 represents a JL7 antigen according to this invention.
Figure 1:
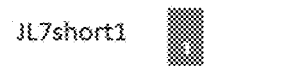
Figure 1:
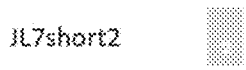
Figure 1:
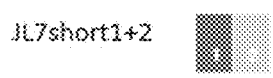
Figure 1:
Figure 1:

These two copies of SEQ ID NO. 2 do not need to be completely identical but both sequences have to show an amino acid identity of at least 90% compared to SEQ ID NO. 2. For example, SEQ ID NO. 4 (JL7short1+2) comprises SEQ ID NO. 2 (JL7short1) and SEQ ID NO. 3 (JL7short2). SEQ ID NO. 2 simply shows 100% amino acid identity to SEQ NO. 2 and SEQ ID NO. 3 has got 66 out of 68 amino acids identical to SEQ ID NO. 2, resulting in a degree of amino acid identity of 97%. As another example, repeat 3 shown in FIG. 1 (SEQ ID NO. 6) has differences in six amino acid positions compared to SEQ ID NO. 2, resulting in 91% amino acid identity (62/68). According to the invention the JL7 polypeptide can therefore comprise an amino acid sequence wherein the JL7 specific portion consists of SEQ ID NOs. 2 and 3 or SEQ ID NO. 2 and 6 or SEQ ID NOs 3 and 6. In a preferred mode the JL7 specific portion consists of SEQ ID NO. 4 which is a combination of SEQ ID NOs 2 and 3.

For the sake of clarity, also a JL7 specific amino acid sequence of a shorter length of 62, 63, 64, 65, 66 or 67 amino acids, wherein all remaining amino acid residues of the shortened JL7 fragment are identical to SEQ ID NO. 2, fulfills the requirement of at least 90% amino acid identity to SEQ ID NO. 2, e.g. 62/68=91%. In another embodiment the requirement of amino acid identity to SEQ ID NO. 2 is at least 95%. Preferably, the deletion of said shortened JL7 fragment concerns N- and C-terminal amino acid residues, leaving the core of the JL7 SEQ ID NO. 2 sequence intact.

It is important that apart from the JL7 specific amino acid sequence no further Trypanosoma cruzi specific amino acid sequences are present in the polypeptides according to the invention. For the sake of clarity, also further JL7 specific amino acid sequences beyond those explicitly described are absent in the polypeptides. Full-length JL7 as disclosed in SEQ ID NO. 1 is therefore not encompassed in the invention. To provide clarity of the invention, also several molecules of e.g. SEQ ID NO. 4 which already harbors two repeats of the sequence motif shown in SEQ ID NO. 2 cannot be present on the same polypeptide chain.

According to the invention also variants of the JL7 antigen are contemplated as long as the prerequisite that the JL7 specific sequence consists of two copies of SEQ ID NO.2, each having an amino acid identity of at least 90% to SEQ ID NO. 2, is fulfilled. In an embodiment said amino acid identity is at least 95% to SEQ ID NO. 2. A variant classifies as such as long as the immunoreactivity in an in vitro diagnostic immunoassay is maintained, i.e. the variant is still able to bind and detect anti-*T. cruzi* antibodies present in a sample. A variant is also a JL7 polypeptide which has been modified for example by covalent attachment of a linker amino acid sequence, a label, a tag, an amino acid sequence or carrier moiety to the polypeptide or antigen. The term "variant" also relates to a post-translationally modified protein such as a glycosylated or phosphorylated protein or to fusion proteins that facilitate cloning, expression, purification and folding.

The terms JL7 variant, JL7 antigen, JL7 polypeptide or JL7 antigenic polypeptide or protein are used synonymously in this specification. Also the terms *Trypanosoma cruzi* (=*T. cruzi*) specific antigen or *T. cruzi* polypeptide are understood as synonyms and each refer to a polypeptide sequence, also referred to as amino acid sequence, that can be found in any naturally occurring *T. cruzi* strain accessible through an international protein sequence database such as UniProt.

Usually in order to detect all stages of a *T. cruzi* infection several different *T. cruzi* antigens are applied in an assay for detecting *T. cruzi* antibodies. A further aspect of the invention is therefore a composition of polypeptides suitable for detecting antibodies against *Trypanosoma cruzi* antigens in an isolated biological sample comprising a JL7 polypeptide as specified above and at least one *Trypanosoma cruzi* polypeptide selected from the group consisting of 1F8, Cruzipain, KMP-11 and PAR-2. Amino acid sequences from these additional antigens are known in prior art and are retrievable from publically available databases such as UniProt; e.g. 1F8 (UniProt entry Q4D1Q2), also known as FCaBP, Tc24 or Tc28; Cruzipain (UniProt entry Q9TW51), also known as Cruzain, gp51/57, Ag 163B6; KMP-11 (UniProt entry Q9U6Z1); PAR2 (UniProt entry Q01530), also known as PFR2.

The term composition means that isolated separate *T. cruzi* polypeptides are combined to an admixture. This term shall not include polypeptides that have been recombinantly expressed or synthesized on one single chain of amino acids so that all polypeptides are located on just one polypeptide chain as a multi-antigen-fusion polypeptide. In other words, multi-epitope fusion antigens of several epitopes that naturally do not appear on a single polypeptide chain are excluded. Rather, each of the additional *T. cruzi* polypeptides 1F8, Cruzipain, KMP-11 and PAR2 are expressed on or chemically synthesized as separate polypeptide chains. The composition is created by mixing the individual *T. cruzi* polypeptides in one vessel or tube resulting in a composition.

The composition can be liquid, i.e. the *T. cruzi* polypeptides are added to a mixture in a water or buffer soluble form. Suitable buffer ingredients are known to the person skilled in the art. Said composition may also be solid, i.e. it comprises the *T. cruzi* antigens in a lyophilized or otherwise dried form.

Moreover the current invention concerns a method of producing a soluble and immunoreactive *Trypanosoma cruzi* JL7 polypeptide as described further above, said method comprising the steps of a) culturing host cells transformed with an expression vector comprising operably linked a recombinant DNA molecule encoding a *Trypanosoma cruzi* JL7 polypeptide, b) expression of said *Trypanosoma cruzi* JL7 polypeptide and c) purification of said *Trypanosoma cruzi* JL7 polypeptide.

Another aspect of the invention is a method for detecting antibodies specific for *Trypanosoma cruzi* in an isolated sample wherein a *Trypanosoma cruzi* JL7 polypeptide as disclosed above or a *Trypanosoma cruzi* JL7 polypeptide obtained by a method defined above or a composition of *Trypanosoma cruzi* polypeptides as just described is used as a capture reagent and/or as a binding partner for said *Trypanosoma cruzi* antibodies.

Yet another embodiment is method for detecting antibodies specific for *Trypanosoma cruzi* in an isolated sample said method comprising a) forming an immunoreaction admixture by admixing a body fluid sample with a Trypanosoma cruzi JL7 polypeptide according to the invention or a composition already described or a *Trypanosoma cruzi* JL7 polypeptide obtained by the method illustrated in a preceding paragraph of this specification b) maintaining said immunoreaction admixture for a time period sufficient for allowing antibodies present in the body fluid sample against said composition of polypeptides sample to immunoreact with said composition of *Trypanosoma cruzi* polypeptides to form an immunoreaction product; and c) detecting the presence and/or the concentration of any of said immunoreaction product.

In a further aspect the immunoassay methods according to the invention are suitable for detecting *T. cruzi* antibodies of all soluble immunoglobulin subclasses, including IgG and IgM as the most relevant subclasses for Chagas diagnostics.

The invention further concerns a method for detecting antibodies specific for *Trypanosoma cruzi* in an isolated sample in a so-called double antigen sandwich format DAGS. Said method for detecting antibodies specific for *Trypanosoma cruzi* in an isolated sample is preferably carried out in a double antigen sandwich (DAGS) format. In such an assay the ability of an antibody to bind at least two different molecules of a given antigen with its two (IgG, IgA, IgE) or ten (IgM) paratopes is required and utilized. In said DAGS immunoassay the basic structures of the "solid phase antigen" and the "detection antigen" are essentially the same so that the sample antibody forms a bridge between two specific antigens. Both antigens therefore have to be either identical or immunologically cross-reactive so that one antibody is able to bind to both antigens. The essential requirement for performing such assays is that the relevant epitope or the relevant epitopes are present on both antigens. One of the two antigens can be bound to a solid phase and the other antigen carries a detectable label.

This method comprises the following steps:

a) adding to an isolated sample sample a first *Trypanosoma cruzi* JL7 polypeptide which can be bound directly or indirectly to a solid phase and said first *Trypanosoma cruzi* polypeptide carries an effector group which is part of a bioaffine binding pair, and a second *Trypanosoma cruzi* JL7 polypeptide and said second *Trypanosoma cruzi* JL7 polypeptide carries a detectable label, wherein said first and second *Trypanosoma cruzi* JL7 polypeptides bind specifically to said anti-*Trypanosoma cruzi* antibodies, b) forming an immunoreaction admixture comprising said first *Trypanosoma cruzi* JL7 polypeptide, said sample antibody and said second *Trypanosoma cruzi* JL7 polypeptide wherein a solid phase carrying a corresponding effector group of said bioaffine binding pair is added before, during or after forming the immunoreaction admixture, c) maintaining said immunoreaction admixture for a time period sufficient for allowing *Trypanosoma cruzi* antibodies against said first and second *Trypanosoma cruzi* JL7 polypeptides in the body fluid sample to immunoreact with said first and second *Trypanosoma cruzi* polypeptides to form an immunoreaction product, d) separating the liquid phase from the solid phase e) detecting the presence of any of said immunoreaction product in the solid or liquid phase or both.

In a preferred mode of the described sandwich method the first *Trypanosoma cruzi* JL7 polypeptide carries a biotin moiety, and the second *Trypanosoma cruzi* JL7 polypeptide is labeled with an electrochemiluminescent ruthenium complex the signal of which can be detected.

The invention also covers the use of a *Trypanosoma cruzi* JL7 polypeptide or of a composition of *T. cruzi* specific polypeptides or of a JL7 polypeptide obtained by a recombinant production method defined above, all described in this specification further above, in an in vitro diagnostic test for the detection of anti-*Trypanosoma cruzi* antibodies.

Another aspect of this invention is a reagent kit for the detection of anti-*Trypanosoma cruzi* antibodies, comprising a *Trypanosoma cruzi* JL7 polypeptide according to the invention or a JL7 polypeptide obtained by the method of production described further above or of a composition of a JL7 polypeptide and at least one additional *T. cruzi* antigens selected from 1F8, Cruzipain, KMP-11 and PAR2.

Said kit is useful for an in vitro diagnostic test for the detection of anti-*Trypanosoma cruzi* antibodies and may further contain controls and standard solutions in separate vials as well as additional reagents in one or more solutions or in lyophilized form with the common additives, buffers, salts, detergents etc. and instructions for use as known by the person skilled in the art.

The invention is further illustrated in the examples section.

EXAMPLE 1

Cloning and Purification of the *Trypanosoma cruzi* JL7 Antigen Variants

In order to investigate the minimal size of the *T. cruzi* JL7 antigen suitable for its application in an immunodiagnostic test several variants consisting of one or two repeat units were generated.

Synthetic genes encoding the *T. cruzi* antigens as listed in table 1 were purchased from Eurofins MWG Operon (Ebersberg, Germany). On the basis of the pET24a expression plasmid of Novagen (Madison, Wis., USA) the following cloning steps were performed. The vector was digested with NdeI and XhoI and a cassette comprising the respective *T. cruzi* antigens were inserted. The insert of the resulting plasmid was sequenced and found to encode the desired protein. The amino acid sequences of the resulting proteins are shown in the sequence protocol of the present invention. All recombinant *T. cruzi* polypeptide variants contained a C-terminal hexahistidine tag (SEQ ID NO. 7) to facilitate Ni-NTA-assisted purification. SEQ ID NOs. are summarized in Table 1.

All *T. cruzi* antigens were purified according to the following protocol. *E. coli* BL21 (DE3) cells harboring the expression plasmid were grown in LB medium plus kanamycin (30 µg/ml) to an $OD_{600}$ of 1, and cytosolic overexpression was induced by adding isopropyl-β-D-thiogalactosid (IPTG) to a final concentration of 1 mM at a growth temperature of 37° C. 4 hours after induction, cells were harvested by centrifugation (20 min at 5000×g), frozen and stored at −20° C. For cell lysis, the frozen pellet was resuspended in 25 mM sodium phosphate pH 8.5, 6 mM $MgCl_2$, 10 U/ml Benzonase®, 1 tablet Complete® and 1 tablet Complete® EDTA-free per 50 ml of buffer (protease inhibitor cocktail) and the resulting suspension was lysed by high pressure homogenization. The crude lysate was supplemented up to 50 mM sodium phosphate, 10 mM imidazole. After centrifugation the supernatant was applied onto a Ni-NTA (nickel-nitrilotriacetate) column pre-equilibrated in buffer A (50 mM sodium phosphate pH 8.5, 100 mM sodium chloride, 10 mM imidazole). Prior to elution, the imidazole concentration was raised to 40 mM in order to remove contaminant proteins. The proteins were then eluted by applying an imidazole concentration of 250 mM. Finally, the proteins were subjected to size exclusion chromatography and the protein-containing fractions was pooled and concentrated.

TABLE 1

Summary *T. cruzi* JL7 antigen variants SEQ ID Nos.

| *T. cruzi* antigen | SEQ ID NO. |
|---|---|
| JL7 | 1 |
| JL7short1 | 2 |

TABLE 1-continued

Summary *T. cruzi* JL7 antigen variants SEQ ID Nos.

| *T. cruzi* antigen | SEQ ID NO. |
|---|---|
| JL7short2 | 3 |
| JL7short1 + 2 | 4 |
| JL7short3 + 4 | 5 |
| JL7short3 | 6 |

EXAMPLE 2

Spectroscopic Measurements

Circular dichroism spectroscopy (CD) is the method of choice to assess the secondary structure in proteins. Ellipticity in the amide region (190-250 nm) reflects regular repetitive elements in the protein backbone, i.e. the secondary structure.

Near-UV CD spectra were recorded with a Jasco-720 spectropolarimeter with a thermostatted cell holder and converted to molar ellipticity. The buffer was 10 mM potassium phosphate pH 7.5. The pathlength was 0.1 cm, the protein concentration was 0.2 mg/ml. The band width was 1 nm, the scanning speed was 50 nm/min at a resolution of 1 nm and the response was 2 s. In order to improve the signal-to-noise ratio, spectra were measured eight timesand averaged.

Figure 2:
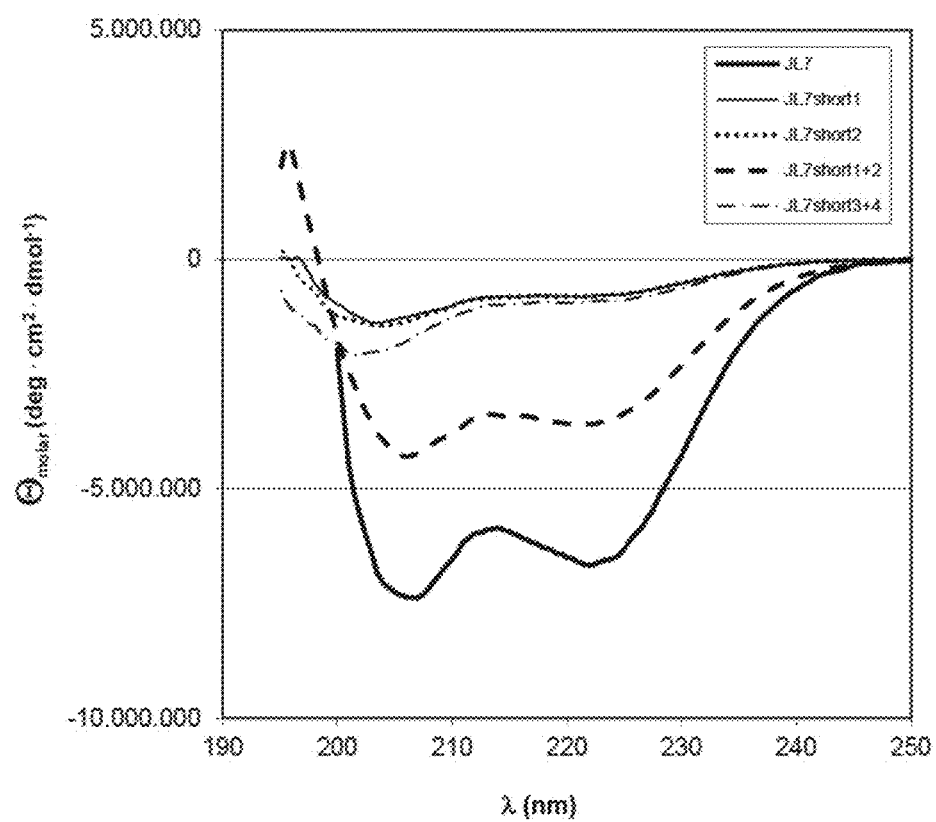
FIG. 2: Far-UV CD spectra of JL7, JL7short1, JL7short2, JL7short1+2 and JL7short3+4. The spectra were recorded on a Jasco-720 spectropolarimeter in a thermostatted cell holder at 20° C. The protein concentration was 0.2 mg/ml in a 0.1 cm cuvette. The buffer was 10 mM potassium phosphate pH 7.5. Band width was 1 nm, resolution was 1 nm, the scanning speed was 50 nm/min at a response of 2 s. Spectra were recorded 8 times and averaged in order to improve the signal-to-noise ratio. The signal was converted to molar ellipticity (given in deg cm$^2$ dmol$^{-1}$). The spectra of JL7 and JL7short1+2 point to proteins with high content of α-helical structural elements (signal bands at 208 nm and 222 nm). The spectra of JL7short1, JL7short2 and JL7short3+4 are indicative for proteins with a high degree of unordered structure (signal band near 200 nm).

FIG. 2 shows far-UV CD spectra of JL7, JL7short1, JL7short2, JL7short1+2 and JL7short3+4. The spectra of JL7 and JL7short1+2 point to proteins with high content of α-helical structural elements (signal bands at 208 nm and 222 nm). The spectra of JL7short1, JL7short2 and JL7short3+4 are indicative for proteins with a high degree of unordered structure (signal band near 200 nm).

The finding that the well-structured variant JL7short1+2 showed the best results in the immunoassay (example 4 and table 2) is therefore consistent. We assume that the shorter variants JL7short1, JL7short2 and JL7short3+4 are not able to maintain a three-dimensional structure that maintains important recognizable epitopes that can be bound by sample antibodies. JL7short1+2 presents relevant epitopes to sample antibodies in a better accessible manner than the shorter variants JL7short1, JL7short2 and JL7short3+4 that do not possess two complete repeats of amino acid sequence SEQ ID NO. 2.

EXAMPLE 3

Coupling of Biotin and Ruthenium Moieties to *T. cruzi* JL7 Antigen Variants

The lysine ε-amino groups of the recombinant proteins were modified at protein concentrations of ~10 mg/ml with N-hydroxy-succinimide activated biotin and ruthenium labels, respectively. The label/protein molar ratio was adjusted to 5:1 and 15:1 for the biotin and ruthenium label conjugation, respectively. The reaction buffer was 50 mM potassium phosphate (pH 8.5), 150 mM KCl, 0.5 mM EDTA. The reaction was carried out at room temperature for 30 minutes and stopped by adding buffered L-lysine to a final concentration of 10 mM. After the coupling reaction, unreacted free label was removed by passing the crude protein conjugate over a gel filtration column (Superdex 200 HI Load).

EXAMPLE 4

Assessment of the Immunological Reactivity and Vulnerability to Interference of the Recombinant *T. cruzi* JL7 Antigen Variants in an Immunodiagnostic Test The immunological reactivity of the different proteins was assessed in an automated cobas® e601 analyzer (Roche Diagnostics GmbH). Measurements were carried out in the double antigen sandwich format. Thereby, the biotin-conjugate (i.e. the capture antigen) is immobilized on the surface of a streptavidin-coated magnetic bead, whereas the detection-antigen bears a complexed ruthenium cation as the signaling moiety. Signal detection in cobas® e601 is based on electrochemiluminescence.

In the presence of a specific immunoglobulin analyte, the chromogenic ruthenium complex is bridged to the solid phase and emits light at 620 nm after excitation at a platinum electrode. The signal output is in arbitrary light units. Measurements were performed with anti-*T. cruzi* positive and negative human serum and plasma samples purchased from several sources.

The recombinant *T. cruzi* JL7 antigen variants according to the invention were assessed pairwise in a double antigen sandwich (DAGS) immunoassay format. For instance, a JL7-biotin conjugate was assessed together with a JL7-ruthenium complex conjugate at a concentration of 100 ng/ml each in assay buffer containing 50 mM MES (pH 6.5), 150 mM NaCl, 0.1% polidocanol, 0.2% bovine albumin, 0.01% N-methylisothiazolon, 0.1% Oxy-Pyrion. The used sample volume was 30 Anti-*T. cruzi* negative human sera were used as controls. Anti-*T. cruzi* positive human sera were used to assess the antigenicity of each variant.

TABLE 2

Detection of anti-*T. cruzi* antibodies in human sera by using recombinant *T. cruzi* JL7 antigen variants

| | JL7 counts | JL7short1 counts | JL7short2 counts | JL7short1 + 2 counts | JL7short3 + 4 counts | bioelisa Chagas |
|---|---|---|---|---|---|---|
| | | | normal samples | | | |
| #1 | 779 | 721 | 664 | 634 | 600 | negative |
| #2 | 714 | 677 | 549 | 507 | 519 | negative |
| #3 | 691 | 600 | 538 | 509 | 521 | negative |
| #4 | 688 | 592 | 553 | 513 | 537 | negative |
| #5 | 706 | 601 | 538 | 509 | 532 | negative |
| mean | 716 | 638 | 568 | 534 | 542 | |
| cut-off (4.5 × mean) | 3'220 | 2'872 | 2'558 | 2'405 | 2'438 | |
| | | | chagas positive samples | | | |
| SN1440-015 | 8'535'719 | 641'038 | 904'786 | 13'345'113 | 30'891 | positive |
| SN1440-021 | 2'606'324 | 644 | 653 | 1'584'540 | 719 | positive |

TABLE 2-continued

Detection of anti-*T. cruzi* antibodies in human sera by using recombinant *T. cruzi* JL7 antigen variants

| | JL7 counts | JL7short1 counts | JL7short2 counts | JL7short1 + 2 counts | JL7short3 + 4 counts | bioelisa Chagas |
|---|---|---|---|---|---|---|
| SN1440-052 | 3'131'565 | 1'429 | 3'487 | 3'807'804 | 744 | positive |
| SN1440-059 | 554'033 | 818 | 1'358 | 394'162 | 721 | positive |
| SN1440-094 | 2'396'405 | 11'031 | 17'289 | 1'801'162 | 650 | positive |
| reactive samples of bavarian blood donors | | | | | | |
| SN1489-006 | 44'066 | 621 | 555 | 495 | 522 | negative |
| SN1489-201 | 3'618 | 606 | 564 | 5'811 | 527 | negative |
| SN1489-237 | 31'562 | 629 | 553 | 2'212 | 2'700 | negative |
| SN1489-553 | 17'161 | 620 | 548 | 14'993 | 535 | negative |

In Table 2, the immunological activity of all *T. cruzi* JL7 antigen variants listed in Table 1 (except for JL7short3) is shown.

All samples of Table 2 were tested with a commercially available Chagas assays (bioelisa Chagas from Biokit S. A.) that use several *T. cruzi* antigens but no JL7 according to the instructions of the manufacturer.

A specificity study comprising blood donors from the Bavarian Red Cross (n=998) revealed 4 samples expected to be false reactive for anti *T. cruzi* antibodies due to the fact that Bavaria (Germany) is not an endemic area of the Chagas disease and also the approved bioelisa Chagas (Biokit S. A.) was non-reactive.

In order to decide whether a sample is reactive or non-reactive a mean background signal was determined (average of negative samples) and a cut-off-value was calculated which was 4.5 times the mean background signal (4.5× mean).

The cut-off value as threshold for determining whether a sample is reactive or non-reactive is chosen individually depending on the assay conditions. Such a procedure is known to a person skilled in the art. In addition, the absolute signal counts can be normalized by deviding the signal counts by the pre-determined cut-off value (data not shown). Thus a positive, i.e. reactive sample would show up as a normalized value of greater than 1 (>1) and results from non-reactive samples would have a value between 0 and 1.

Turning to Table 2, it is obvious that the reactivity of the *T. cruzi* JL7 antigen variants is strongly dependent on the number of complete repeat units. So the isolated repeat unit 1 or 2 and the fused repeat units 3 with the shortened unit 4 showed significant reduced antigenicity. Its vulnerability to interference seems to be at once strongly diminished. In contrast to this, the fusion of two complete repeat units as in the case of the variant JL7short1+2 maintains the entire antigenicity as in the complete JL7 molecule and at the same time identifies negative and positive samples correctly. Two out of four interference samples showed a significant reduction of the measured signals. Use of a JL7 variant wherein the JL7 specific part consists of only two repeats of SEQ ID NO. 2 (and variants with at least 90% or in an embodiment with at least 95% amino acid sequence identity to it) increases the specificity of an anti-*T. cruzi* immunoassay considerably.

The invention claimed is:

1. A polypeptide suitable for detecting antibodies against *Trypanosoma cruzi* in an isolated biological sample comprising *Trypanosoma cruzi* JL7 specific amino acid sequence consists of SEQ ID NO. 4, and wherein no further *Trypanosoma cruzi* specific amino acid sequences are present in said polypeptide.

2. A composition of polypeptides suitable for detecting antibodies against *Trypanosoma cruzi* antigens in an isolated biological sample comprising a polypeptide according to claim 1 and at least one *Trypanosoma cruzi* polypeptide selected from the group consisting of 1F8, Cruzipain, KMP-11 and PAR-2.

3. A reagent kit for the detection of anti-*Trypanosoma cruzi* antibodies, comprising a *Trypanosoma cruzi* JL7 polypeptide according to claim 1 or of a composition according to claim 2.

* * * * *